(12) United States Patent
Cawse

(10) Patent No.: US 6,684,161 B2
(45) Date of Patent: Jan. 27, 2004

(54) COMBINATORIAL EXPERIMENT DESIGN METHOD AND SYSTEM

(75) Inventor: James Norman Cawse, Pittsfield, MA (US)

(73) Assignee: General Electric Company, Niskayuna, NY (US)

( * ) Notice: Subject to any disclaimer, the term of this patent is extended or adjusted under 35 U.S.C. 154(b) by 336 days.

(21) Appl. No.: 09/682,029

(22) Filed: Jul. 11, 2001

(65) Prior Publication Data

US 2003/0013207 A1 Jan. 16, 2003

(51) Int. Cl.[7] .................. G06F 19/00; G11C 17/00; C12M 1/36
(52) U.S. Cl. .................. 702/22; 700/1; 435/286.4
(58) Field of Search .................. 702/22; 700/1; 435/286.4

(56) References Cited

U.S. PATENT DOCUMENTS

| | | |
|---|---|---|
| 5,917,077 A | 6/1999 | Chaudhari et al. |
| 6,045,671 A | 4/2000 | Wu et al. |
| 6,048,469 A | 4/2000 | Xiang et al. |
| 6,114,563 A | 9/2000 | Spivack et al. |
| 6,143,913 A | 11/2000 | Spivack et al. |
| 6,143,914 A | 11/2000 | Spivack et al. |

OTHER PUBLICATIONS

Thomas E. Mallouk et al., Science, vol. 280, pp. 1735–1737 (1998).
Kreher (D. L. Kreher, ▌ t–Designs, t =3,▌ in The CRC Handbook of Combinatorial Designs, C.J. Colbourn and J.H. Dinitz, eds, CRC Press, New York, 47–65 1996).
R. J. Degray, ▌ Design for Interactions,▌ Technometrics 10(2), 389–391, 1968.
Alfred Wasserman, Finding Simple t–Designs with Enumeration Techniques, Journal of Combinatorial Designs, 6, 2 (1998), pp. 79–90.

Primary Examiner—John S. Brusca
(74) Attorney, Agent, or Firm—Andrew J. Caruso; Patrick K. Patnode

(57) ABSTRACT

An experimental space comprising levels of factors is designed according to an incomplete block design and an experimental space comprising levels of factors is designed by random selection. Separate combinatorial high throughput screening experiments are effected on each experimental space to produce sets of results and best results are selected from the sets. A system for conducting an experiment includes a reactor for effecting a combinatorial high throughput screening method on an experimental space to produce results and a programmed controller that defines an experimental space comprising levels of factors according to an incomplete block design and defines an experimental space comprising levels of factors by random selection.

34 Claims, 1 Drawing Sheet

COMBINATORIAL EXPERIMENT DESIGN METHOD AND SYSTEM

BACKGROUND OF INVENTION

The present invention relates to a combinatorial high throughput screening (CHTS) experiment design method and system.

Combinatorial organic synthesis (COS) is an HTS methodology that was developed for pharmaceuticals. COS uses systematic and repetitive synthesis to produce diverse molecular entities formed from sets of chemical "building blocks." As with traditional research, COS relies on experimental synthesis methodology. However instead of synthesizing a single compound, COS exploits automation and miniaturization to produce large libraries of compounds through successive stages, each of which produces a chemical modification of an existing molecule of a preceding stage. A library is a physical, trackable collection of samples resulting from a definable set of processes or reaction steps. The libraries comprise compounds that can be screened for various activities.

For a number of reasons, it is difficult to apply the methodology of COS to catalyzed chemical reactions. First, chemical reactions particularly industrial catalyzed chemical reactions can involve large numbers of factors and require investigation of enormous numbers of factor levels (settings). For example, even a simple commercial process may involve five or six critical factors, each of which can be set at 2 to 20 levels. A complex homogeneous catalyst system may involve two, three, or even more metal cocatalysts that can synergistically combine to improve the overall rate of the process. These cocatalysts can be chosen from a large list of candidates. Additional factors can include reactants and processing conditions. The number of tertiary, 4-way, 5-way, and 6-way factor combinations can rapidly become extremely large, depending on the number of levels for each factor.

Another problem is that catalyzed chemical reactions are unpredictable. T. E. Mallouk et al. in Science, 1735 (1998) shows that effective ternary combinations can exist in systems in which no binary combinations are effective. Accordingly, it may be necessary to search enormous numbers of combinations to find a handful of leads," i.e., combinations that may lead to commercially valuable applications.

One answer to this problem is to carefully select and organize the experimental space of the system. However in this respect, the challenge is to define a reasonably sized experimental space that will provide meaningful results. There is a need for an experimental protocol to specify arrangements of formulations and processing conditions for combinatorial high through put screening (CHTS) so that positive interactions of formulation and processing variables can be reliably and efficiently detected.

SUMMARY OF INVENTION

The present invention relates to an experimental design strategy for evaluating systems with complex physical, chemical and structural requirements by CHTS. The definition of the experimental space permits a CHTS reliable and efficient investigation of highly complex systems. In the method, an experimental space comprising levels of factors is designed according to an incomplete block design and an experimental space comprising levels of factors is designed by random selection. Separate CHTS experiments are effected on each experimental space to produce sets of results and best common results are selected from the sets.

In an embodiment, the invention relates to a CHTS method comprising (1) selecting factors for an experimental space, (2) selecting a degree of interaction (t) of the factors, (3) selecting a degree of replication ($\lambda$), (4) selecting a block size ($\kappa$), (5) generating an experimental incomplete block design according to t, $\lambda$ and $\kappa$, (6) conducting a CHTS method according to the design, (7) randomly permuting levels of the factors in the design, (8) conducting a second CHTS method according to the permuted levels design and (9) identifying common levels from the experiments that represent best results.

The invention also relates to a system for conducting an experiment. The system comprises a reactor for effecting a CHTS method on an experimental space to produce results and a programmed controller for the reactor that defines an experimental space comprising levels of factors according to an incomplete block design and defines an experimental space comprising levels of factors by random selection.

DETAILED DESCRIPTION

Figure 1:
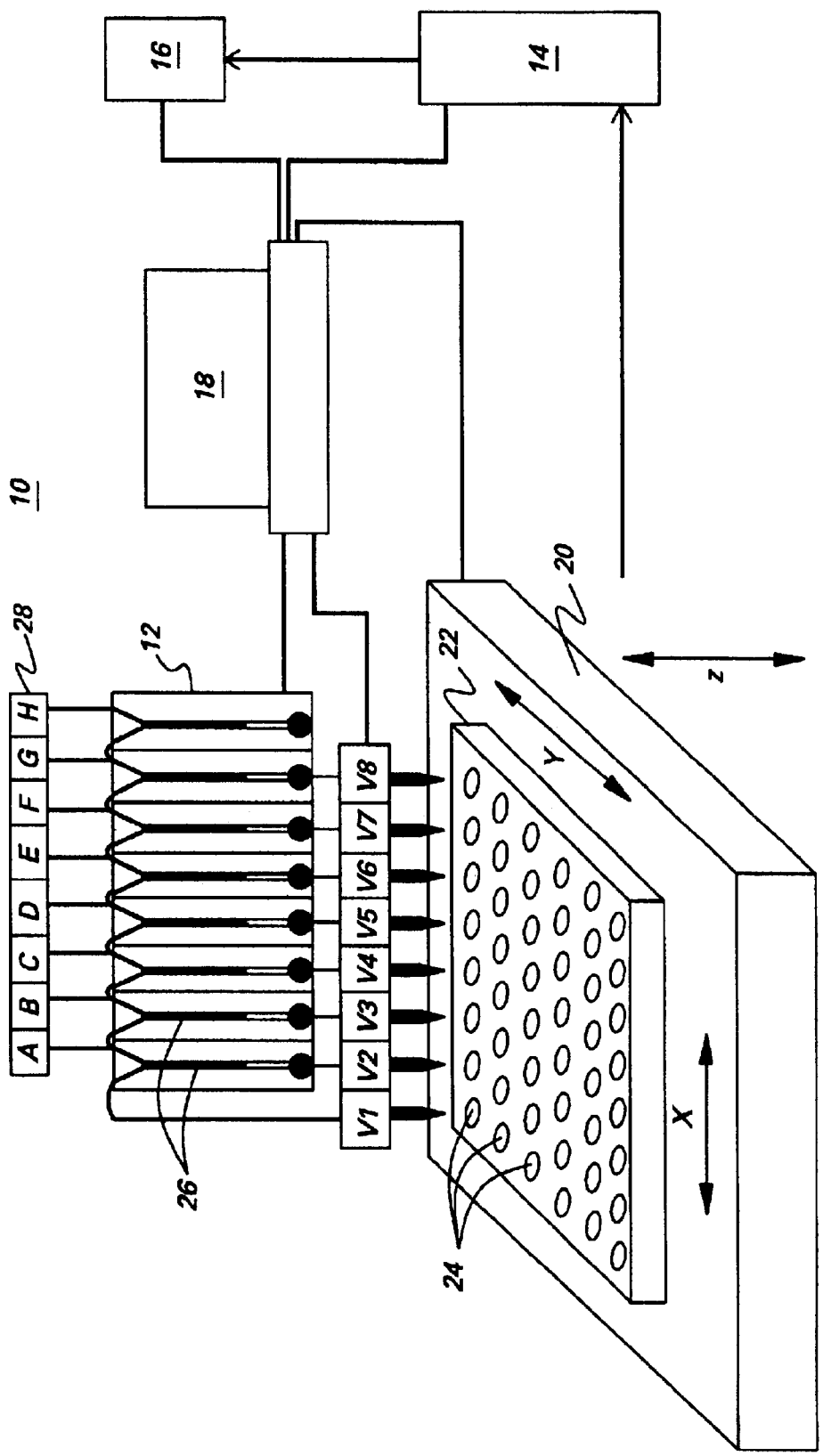
FIG. 1 is a schematic representation of a system and method for conducting a CHTS experiment.

The object of a chts experiment is to determine purposeful input variables of a process or system so that reasons for changes in an output response can be observed and identified. CHTS is an HTS methodology that incorporates characteristics of COS. The steps of a CHTS methodology can be broken down into generic operations including selecting chemicals to be used in an experiment; introducing the chemicals into a formulation system (typically by weighing and dissolving to form stock solutions), combining aliquots of the solutions into formulations or mixtures in a geometrical array (typically by the use of a pipetting robot); processing the array of chemical combinations into products and analyzing properties of the products. Results from the analyzing step can be used to compare properties of the products in order to discover "leads" materials whose properties indicate commercial potential.

Typically, CHTS methodology is characterized by parallel reactions at a micro scale. In one aspect, CHTS can be described as a method comprising (A)an iteration of steps of (i) selecting a reactant, catalyst or condition set; (ii) reacting the set; and (iii) evaluating products of the reacting step; and (B) reiterating step (A) wherein a successive reactant, catalyst or condition set selected for a step (i) is chosen as a result of an evaluating step (iii) of a preceding iteration.

In another CHTS method, a multiplicity of tagged reactants is subjected to an iteration of steps of (A) (i) simultaneously reacting the reactants, (ii) identifying a multiplicity of tagged products of the reaction and (B) evaluating the identified products after completion of a single or repeated iteration (A). A CHTS can utilize advanced automated, robotic, computerized and controlled loading, reacting and evaluating procedures.

In one CHTS method, the reactant or catalyst is at least partially embodied in a liquid and effecting the CHTS method comprises contacting the reactant or catalyst with an additional reactant at least partially embodied in a gas, wherein the liquid forms a film having a thickness sufficient to allow a reaction rate that is essentially independent of a mass transfer rate of additional reactant into the liquid to synthesize products that comprise the results.

According to the invention, a methodology is applied to define two different experimental spaces for two different iterations of a CHTS method. A first space is defined with levels according to an incomplete block design. A second experimental space is designed by random selection. Results from the CHTS method on the first space and results from the CHTS method on the randomly selected space are compared and best common results are selected from the compared results. These common results can be best results for the experiment or they can be used to define subsequent iterations of the CHTS method. Surprising, the comparing of results and selecting of common best results can effectively identify best results in a lesser number of iterations than other CHTS definitional methodologies.

An incomplete block design is a set of v elements (which for example may be factors or levels of factors for a CHTS experiment arranged into κ-size subsets (or blocks) of the v elements that contain all t-size subsets of the v elements. These designs may be Latin squares (see Cawse R D-28249, incorporated herein by reference in its entirety), t-designs, or other incomplete block designs known to those skilled in the art. T-designs are one of the most efficient of these designs. Kreher (D. L. Kreher, t-Designs, t=3," in The CRC Handbook of Combinatorial Designs, C. J. Colbourn and J. H. Dinitz, eds, CRC Press, New York, 47–65, 1996) shows t-designs for large numbers of factor levels. The levels are divided into a group of subsets called blocks in such a way that every subset of t points is contained in precisely the same number of blocks.

R. J. Degray, "Design for Interactions," Technometrics 10(2), 389–391, 1968, teaches a simple design where effective members of an interaction can be determined by a "leave out one" approach. Thus if there are 7 candidate variables A–G, according to an hypothesis, a critical interaction can be located by running 7 experiments, leaving out one candidate each time. The design is illustrated in TABLE 1.

TABLE 1

| 1 | ABCDEF |
| 2 | ABCDEG |
| 3 | ABCDFG |
| 4 | ABCEFG |
| 5 | ABDEFG |
| 6 | ACDEFG |
| 7 | BCDEFG |

This design in effect tests all combinations of one to six of the factors. If the interaction is indeed critical, leaving out any factor in it will markedly change the result of the experiment. Thus each run of the seven that is markedly different from the others will indicate the presence of a flevel of the critical interaction. For example, if both 5) and 7) show a decreased response, C and A may be involved in a critical interaction.

In t-design terminology t-(v, κ, λ), t is the size of an interaction subset (e.g., t=3 for a 3-way interaction); v is a total number of levels in the design (e.g. candidates in the formulation and process), κ is block size and λ is the number of times each t-size subset is contained in the total set of blocks. In the preferred designs, t can about 3 to about 4; v can be about 14 to about 26; κ can be about 4 to about 6; and λ can be about 1 to about 2. All 3-way or 4-way combinations of a group of more than 10 candidates can be investigated through formulation or process levels of less than seven candidates. It is preferred to limit the combinations of candidates to one or two replicates. The following TABLE 2 shows broad, desired and preferred parameter combinations.

TABLE 2

| Parameter | Broad | Desired | Preferred |
|---|---|---|---|
| τ | 3–5 | 3–4 | |
| v | 8–100 | 10–30 | 14–26 |
| κ | 4–10 | 4–8 | 4–6 |
| λ | 1–5 | 1–3 | 1–2 |

In an embodiment of the t-design, a set of κ-sized blocks is specified that will contain all t-size subsets exactly once each. An example is shown in the following TABLE 3 where t=3, v=8, κ=4 and A, B, C, D, E, F, G, and H are ingredients which are candidates for a formulation. The TABLE 3 design illustrates a situation where an experimenter desires to examine the effect of any three of eight candidate ingredients. If each 3-way combination were tested individually, the number of experiments would be Choose(8,3)=56. Since 4-way combinations contain Choose (4,3)=4 3-way combinations, Choose(8.3)/Choose(4,3)=14 4-way combinations can be selected to test all 56 3-way combinations.

TABLE 3

| κ-sized blocks (κ = 4) | t-sized subsets (t = 3) | | | |
|---|---|---|---|---|
| ABCD | ABC | ABD | ACD | BCD |
| ABEF | ABE | ABF | AEF | BEF |
| ABGH | ABG | ABH | AGH | BGH |
| ACEG | ACE | ACG | AEG | CEG |
| ACFH | ACF | ACH | AFH | CFH |
| ADEH | ADE | ADH | AEH | DEH |
| ADFG | ADF | ADG | AFG | DFG |
| BCEH | BCE | BCH | BEH | CEH |
| BCFG | BCF | BCG | BFG | CFG |
| BDEG | BDE | BDG | BEG | DEG |
| BDFH | BDF | BDH | BFH | DFH |
| CDEF | CDE | CDF | CEF | DEF |
| CDGH | CDG | CDH | CGH | DGH |
| EFGH | EFG | EFH | EGH | FGH |

Various other t-designs can be constructed by methods such as enumeration (Alfred Wasserman, Finding Simple t-Designs with Enumeration Techniques, *Journal of Combinatorial Designs*, 6, 2 (1998), pp. 79–90), which is incorporated herein by reference in its entirety.

An embodiment of the invention comprises (1) selecting factors for an experimental space, (2) selecting a degree of interaction (t) of the factors, (3) selecting a degree of replication (λ), (4) selecting a block size (κ), (5) generating an experimental incomplete block design according to t, λ and κ, (6) conducting the experiment according to the design, (7) randomly permuting levels of the factors in the design, (8) conducting a second experiment according to the permuted levels design and (9) identifying common levels from the experiments that represent best results. In one embodiment, the common levels can be identified by arranging the results of the two experiments in such a way that possible "lead" interactions can be easy identified. For example, the results can be arranged in a visual aid such as converging vectors that represent results from the two experiments or as an array that displays common best results in a designated array section.

In the first step, a set of factor levels of the experimental space is selected based on chemical judgment that the levels may interact with each other to effect a desired outcome. These factors can be formulation factors and process factors.

The factors are represented by +1 or 0, a yes or no code that indicates whether the factor is present in an experiment definition or not. In a next step, a degree of interaction among the factors, which the experimenter desires to study (t), is selected. The degree of interaction may be equivalent to the n-value where the improvement is expected to be the result of an n-way combination of the factors. A block size (κ) is selected. The block size is equal to the number of factors that will be tested simultaneously in each experimental run.

Formulations equivalent to the blocks identified are made up as a CHTS experimental array. If process factors are being investigated, the runs must be sorted by process factor and set up as separate arrays for each 0 or 1 setting of the process factors. The experiment is run. A second run of the t-design is prepared, but levels of the factors are randomly permuted. Thus, for example, from Table 3 above, A,B,C, D,E,F are identified as the elements Cr, Ce, Fe, Mn, Ru, and Ir respectively in the first run. In the second run A,B,C,D,E,F are identified as Mn, Ru, Fe, Ce, Ir and Cr. The formulations and example outcomes from each run can be represented as in TABLE 4.

TABLE 4

|  | Run 1 Formulation | Run 1 Outcome | Run 2 Formulation | Run 2 Outcome |
| --- | --- | --- | --- | --- |
| ABCD | Cr,Ce,Fe,Mn | 560 | Mn,Ru,Fe,Ce | 1190 |
| ABEF | Cr,Ce,Ru,Ir | 780 | Mn,Ru,Ir,Cr. | 1300 |
| ADEF | Cr,Mn,Ru,Ir | 1090 | Mn,Ce,Ir,Cr | 260 |
| ACEF | Cr,Fe,Ru,Ir | 350 | Mn,Fe,Ir,Cr | 580 |
| BDEF | Ce,Fe,Ru,Ir | 650 | Ru,Ce,Ir,Cr | 490 |
| BCEF | Ce,Fe,Ru,Ir | 700 | Ru,Fe,Ir,Cr | 720 |
| CDEF | Fe,Mn,Ru,Ir | 1200 | Fe,Ce,Ir,Cr | 380 |

The results of the two runs can be compared by identifying positive results (leads) according to a normal probability plot. The null hypothesis is applied in this identification. The null hypothesis is that all of the effects observed in the experiment are caused simply by random processes. If this is correct, the effects will fit to a normal distribution and form a relatively straight line in a probability plot. A desired standard deviation can be selected by an experimenter for the experiment. Any effects that fall off the line by more than the standard deviation can be interpreted to have been caused by nonrandom processes, as taught by D. Montgomery, Design and Analysis of Experiments, $3^{rd}$ Ed., John Wiley, 1991, N.Y., p 99. These effects can be the leads of interest.

Best common results are then selected from the first specified design and from the second randomized design. A comparison array can be used as a visual aid to select the best common results. In this procedure, the specified t-design results can be arranged horizontally across the top of the array and the random design results can be placed vertically on the left of the array with best results at the top. An intersecting array cell will include the best common results.

These and other features will become apparent from the drawing and following detailed discussion, which byway of example without limitation describe preferred embodiments of the present invention.

FIG. 1 is a schematic representation of a system 10 and method for conducting a CHTS experiment. FIG. 1 shows system 10 including dispensing assembly 12, reactor 14, detector 16 and controller 18. Further shown, is X-Y-Z robotic positioning stage 20, which supports array plate 22 with wells 24. The dispensing assembly 12 includes a battery of pipettes 26 that are controlled by controller 18. X-Y-Z robotic positioning stage 20 is controlled by controller 18 to position wells 24 of the array plate 22 beneath displacement pipettes 26 for delivery of test solutions from reservoirs 28.

Controller 18 can include a data base repository for storing specified t-design inputs from an experimenter. The controller can include algorithms or programs for specifying the randomly defined design as well. The controller 18 also controls aspiration of precursor solution into the battery of pipettes 26 and sequential positioning of the wells 24 of array plate 22 so that a prescribed stoichiometry and/or composition of reactant and/or catalyst can be delivered to the wells 24. By coordinating activation of the pipettes 26 and movement of plate 22 on the robotic X-Y-Z stage 20, a library of materials can be generated in a two-dimensional array for use in the CHTS method. Also, the controller 18 can be used to control sequence of charging of sample to reactor 14 and to control operation of the reactor 14 and the detector 16. Controller 18 can be a computer, processor, microprocessor or the like.

The incomplete block experimental space and the random experimental space of the invention can be defined according to constructs that can be embodied as programs resident in controller 18. Controller 18 specifies the spaces according to any requirements that may be input by an experimenter and the spaces are then translated into loading specifications for array plates 33. Then controller 18 controls the operation of pipettes 26 and stage 20 according to the specifications to deliver reactant and/or catalyst to the wells 34 of plates 22.

Additionally, the controller 18 controls the sequence of charging array plate 22 into the reactor 14, which is synchronized with operation of detector 16. Detector 16 detects products of reaction in the wells 24 of array plate 22 after reaction in reactor 14. Detector 16 can utilize chromatography, infra red spectroscopy, mass spectroscopy, laser mass spectroscopy, microspectroscopy, NMR or the like to determine the constituency of each reaction product. The controller 18 uses data on the sample charged by the pipettes 26 and on the constituency of reaction product for each sample from detector 16 to correlate a detected product with at least one varying parameter of reaction.

As an example, if the method and system of FIG. 1 is applied to study a carbonylation catalyst and/or to determine optimum carbonylation reaction conditions, the detector 16 analyzes the contents of the well for carbonylated product. In this case, the detector 16 can use Raman spectroscopy. The Raman peak is integrated using the analyzer electronics and the resulting data can be stored in the controller 18. Other analytical methods may be used—for example, Infrared spectrometry, mass spectrometry, headspace gas-liquid chromatography and fluorescence detection.

In one embodiment, the invention is applied to study a process for preparing diaryl carbonates. Diaryl carbonates such as diphenyl carbonate can be prepared by reaction of hydroxyaromatic compounds such as phenol with oxygen and carbon monoxide in the presence of a catalyst composition comprising a Group VIIIB metal such as palladium or a compound thereof, a bromide source such as a quaternary ammonium or hexaalkylguanidinium bromide and a polyaniline in partially oxidized and partially reduced form. The invention can be applied to screen for a catalyst to prepare a diaryl carbonate by carbonylation.

Various methods for the preparation of diaryl carbonates by a carbonylation reaction of hydroxyaromatic compounds with carbon monoxide and oxygen have been disclosed. The carbonylation reaction requires a rather complex catalyst. Reference is made, for example, to Chaudhari et al., U.S. Pat. No. 5,917,077. The catalyst compositions described therein comprise a Group VIIIB metal (i.e., a metal selected from the group consisting of ruthenium, rhodium, palladium, osmium, iridium and platinum) or a complex thereof.

The catalyst material also includes a bromide source. This may be a quaternary ammonium or quaternary phosphonium bromide or a hexaalkylguanidinium bromide. The guanidinium salts are often preferred; they include the α, ω-T-bis (pentaalkylguanidinium)alkane salts. Salts in which the alkyl groups contain 2–6 carbon atoms and especially tetra-n-butylammonium bromide and hexaethylguanidinium bromide are particularly preferred.

Other catalytic constituents are necessary in accordance with Chaudhari et al. The constituents include inorganic cocatalysts, typically complexes of cobalt(II) salts with organic compounds capable of forming complexes, especially pentadentate complexes. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkylethylenediamines; crown ethers; aromatic or aliphatic amine ethers such as cryptanes; and Schiff bases. The especially preferred inorganic cocatalyst in many instances is a cobalt(II) complex with bis-3-(salicylalamino)propylmethylamine.

Organic cocatalysts may be present. These cocatalysts include various terpyridine, phenanthroline, quinoline and isoquinoline compounds including 2,2':6',2"-terpyridine, 4-methylthio-2,2':6',2"-terpyridine and 2,2':6',2"-terpyridine N-oxide,1,10-phenanthroline, 2,4,7,8-tetramethyl-1,10-phenanthroline, 4,7-diphenyl-1,10, phenanthroline and 3,4,7,8-tetramethy-1,10-phenanthroline. The terpyridines and especially 2,2':6',2"-terpyridine are preferred.

Another catalyst constituent is a polyaniline in partially oxidized and partially reduced form.

Any hydroxyaromatic compound may be employed. Monohydroxyaromatic compounds, such as phenol, the cresols, the xylenois and p-cumylphenol are preferred with phenol being most preferred. The method may be employed with dihydroxyaromatic compounds such as resorcinol, hydroquinone and 2,2-bis(4-hydroxyphenyl)propane or "bisphenol A," whereupon the products are polycarbonates.

Other reagents in the carbonylation process are oxygen and carbon monoxide, which react with the phenol to form the desired diaryl carbonate.

The following Example is illustrative and should not be construed as a limitation on the scope of the claims unless a limitation is specifically recited.

exampleThis example illustrates an identification of an active and selective catalyst for the production of aromatic carbonates. The procedure identifies the best catalyst from a complex chemical space, where the chemical space is defined as an assemblage of all possible experimental conditions defined by a set of variable parameters such as formulation ingredient identity or amount or process reaction time, temperature, or pressure. The chemical space consists of the following TABLE 5 chemical components and TABLE 6 process parameters:

TABLE 5

| Factor | Possible Identities | Concentration |
| --- | --- | --- |
| Primary Catalyst | Pd(acac)2 | 25 ppm |
| Metal Cocatalyst | Mn(acac)2 | 1500 ppm |
| | Fe(acac)3 | |
| | Co(acac)2 | |
| | Ce(acac)3 | |
| | [22 total] | |
| Anion Cocatalyst | hexamethylguanadinium bromide | 5000 ppm |

TABLE 6

| Factor | Levels |
| --- | --- |
| Pressure | 1000 psi, (8% Oxygen in Carbon Monoxide) |
| Temperature | 100 C |
| Reaction time | 180 min |

This experiment is characterized by Choose(22,3)=1540 possible 3-way combinations. This is too large an experiment for available resources. Instead, a t-design with t=3, κ=6, and =1 is chosen for a first run. The t-design is a 77 run experiment, which is shown as the Run 1 section of TABLE 7. Run 2 is a space of randomly selected levels.

TABLE 7

| | Run 1 | | | | | | | Run 2 | | | | | | |
| --- | --- | --- | --- | --- | --- | --- | --- | --- | --- | --- | --- | --- | --- | --- |
| | Cocatalysts | | | | | | TON | | Cocatalysts | | | | | TON |
| 1 | Re | Yb | Ni | Co | Cr | Cs | 210 | 1 | Mn | Cs | Ce | Co | Yb | Cd | 890 |
| 2 | In | Ru | Fe | Ce | Cr | Cs | 1750 | 2 | Re | Ru | Fe | La | Yb | Cd | 1310 |
| 3 | Ca | Cd | La | Bi | Cr | Cs | 290 | 3 | Ir | Bi | Cu | Eu | Yb | Cd | 930 |
| 4 | Rh | Ir | Gd | Cu | Cr | Cs | 500 | 4 | Cr | In | Ca | Rh | Yb | Cd | 500 |
| 5 | Zn | Ti | Mn | Eu | Cr | Cs | 1130 | 5 | Zn | Ti | Ni | Gd | Yb | Cd | 820 |
| 6 | Cd | Ru | Rh | Ni | Mn | Cs | 570 | 6 | Bi | Ru | Cr | Ce | Ni | Cd | 440 |
| 7 | Mn | La | Gd | Ce | Co | Cs | 590 | 7 | Ni | Cu | Ca | La | Co | Cd | 610 |
| 8 | Zn | Ru | Ir | Bi | Co | Cs | 100 | 8 | Zn | Ru | In | Eu | Co | Cd | 320 |
| 9 | Cd | Ti | Fe | Cu | Co | Cs | 850 | 9 | Bi | Ti | Fe | Rh | Co | Cd | 560 |
| 10 | In | Ca | Rh | Eu | Co | Cs | 310 | 10 | Re | Ir | Cr | Gd | Co | Cd | 340 |
| 11 | Yb | Ti | Rh | Bi | Ce | Cs | 1380 | 11 | Cs | Ti | Cr | Eu | La | Cd | 860 |
| 12 | Ca | Zn | Ni | Cu | Ce | Cs | 980 | 12 | Ir | Zn | Ce | Rh | La | Cd | 900 |
| 13 | Cd | Re | Ir | Eu | Ce | Cs | 450 | 13 | Bi | Mn | In | Gd | La | Cd | 2050 |
| 14 | In | Re | Mn | Cu | Bi | Cs | 1140 | 14 | Re | Mn | Ni | Rh | Eu | Cd | 570 |
| 15 | Ni | Gd | Fe | Eu | Bi | Cs | 1440 | 15 | Ce | Ca | Fe | Gd | Eu | Cd | 1470 |
| 16 | Yb | Ru | La | Eu | Cu | Cs | 250 | 16 | Cs | Ru | Cu | Gd | Rh | Cd | 1040 |
| 17 | Re | Zn | Rh | La | Fe | Cs | 1390 | 17 | Mn | Zn | Cr | Cu | Fe | Cd | 1180 |
| 18 | Ca | Yb | Mn | Ir | Fe | Cs | 650 | 18 | Ir | Cs | Ni | In | Fe | Cd | 990 |

TABLE 7-continued

| | Run 1 | | | | | | | Run 2 | | | | | | |
|---|---|---|---|---|---|---|---|---|---|---|---|---|---|---|
| | Cocatalysts | | | | | | TON | Cocatalysts | | | | | | TON |
| 19 | Ca | Re | Ti | Ru | Gd | Cs | 980 | 19 | Ir | Mn | Ti | Ru | Ca | Cd | 1300 |
| 20 | In | Cd | Zn | Yb | Gd | Cs | 470 | 20 | Re | Bi | Zn | Cs | Ca | Cd | 170 |
| 21 | In | Ti | Ni | La | Ir | Cs | 1060 | 21 | Re | Ti | Ce | Cu | In | Cd | 1050 |
| 22 | In | Yb | Rh | Mn | La | Cr | 770 | 22 | Re | Cs | Cr | Ni | Cu | Yb | 1040 |
| 23 | Cd | Zn | Rh | Ce | Co | Cr | 910 | 23 | Bi | Zn | Cr | La | Co | Yb | 210 |
| 24 | In | Ti | Gd | Bi | Co | Cr | 1020 | 24 | Re | Ti | Ca | Eu | Co | Yb | 350 |
| 25 | Ca | Ru | Mn | Cu | Co | Cr | 460 | 25 | Ir | Ru | Ni | Rh | Co | Yb | 170 |
| 26 | La | Ir | Fe | Eu | Co | Cr | 320 | 26 | Cu | In | Fe | Gd | Co | Yb | 640 |
| 27 | Ni | Mn | Ir | Bi | Ce | Cr | 1040 | 27 | Ce | Ni | In | Eu | La | Yb | 850 |
| 28 | Re | Ti | La | Cu | Ce | Cr | 870 | 28 | Mn | Ti | Cu | Rh | La | Yb | 1580 |
| 29 | Ca | Yb | Gd | Eu | Ce | Cr | 640 | 29 | Ir | Cs | Ca | Gd | La | Yb | 290 |
| 30 | Zn | Yb | Fe | Cu | Bi | Cr | 1020 | 30 | Zn | Cs | Fe | Rh | Eu | Yb | 1070 |
| 31 | Re | Ru | Rh | Eu | Bi | Cr | 170 | 31 | Mn | Ru | Cr | Gd | Eu | Yb | 640 |
| 32 | In | Cd | Ni | Eu | Cu | Cr | 530 | 32 | Re | Bi | Ce | Gd | Rh | Yb | 840 |
| 33 | Ca | Ti | Rh | Ni | Fe | Cr | 550 | 33 | Ir | Ti | Cr | Ce | Fe | Yb | 380 |
| 34 | Cd | Re | Mn | Gd | Fe | Cr | 580 | 34 | Bi | Mn | Ni | Ca | Fe | Yb | 2260 |
| 35 | Zn | Ru | Ni | La | Gd | Cr | 230 | 35 | Zn | Ru | Ce | Cu | Ca | Yb | 1660 |
| 36 | Cd | Yb | Ti | Ru | Ir | Cr | 750 | 36 | Bi | Cs | Ti | Ru | In | Yb | 1930 |
| 37 | In | Ca | Re | Zn | Ir | Cr | 350 | 37 | Re | Ir | Mn | Zn | In | Yb | 470 |
| 38 | In | Cd | Re | Ru | La | Co | 280 | 38 | Re | Bi | Mn | Ru | Cu | Co | 1550 |
| 39 | Ca | Zn | Yb | Ti | La | Co | 380 | 39 | Ir | Zn | Cs | Ti | Cu | Co | 1390 |
| 40 | Ca | Re | Fe | Bi | Ce | Co | 920 | 40 | Ir | Mn | Fe | Eu | La | Co | 330 |
| 41 | In | Yb | Ir | Cu | Ce | Co | 440 | 41 | Re | Cs | In | Rh | La | Co | 400 |
| 42 | Ti | Ru | Ni | Eu | Ce | Co | 470 | 42 | Ti | Ru | Ce | Gd | La | Co | 1440 |
| 43 | Rh | Ni | La | Cu | Bi | Co | 200 | 43 | Cr | Ce | Cu | Rh | Eu | Co | 890 |
| 44 | Cd | Yb | Mn | Eu | Bi | Co | 1840 | 44 | Bi | Cs | Ni | Gd | Eu | Cu | 130 |
| 45 | Re | Zn | Gd | Eu | Cu | Co | 450 | 45 | Mn | Zn | Ca | Gd | Rh | Co | 400 |
| 46 | In | Zn | Ni | Mn | Fe | Co | 210 | 46 | Re | Zn | Ce | Ni | Fe | Co | 350 |
| 47 | Yb | Ru | Rh | Gd | Fe | Co | 130 | 47 | Cs | Ru | Cr | Ca | Fe | Co | 390 |
| 48 | Ca | Cd | Ni | Ir | Gd | Co | 200 | 48 | Ir | Bi | Ce | In | Ca | Co | 1030 |
| 49 | Re | Ti | Rh | Mn | Ir | Co | 110 | 49 | Mn | Ti | Cr | Ni | In | Co | 130 |
| 50 | Re | Zn | Yb | Ru | Mn | Ce | 970 | 50 | Mn | Zn | Cs | Ru | Ni | La | 830 |
| 51 | In | Ca | Cd | Ti | Mn | Ce | 1250 | 51 | Re | Ir | Bi | Ti | Ni | La | 850 |
| 52 | Cd | Ru | Gd | Cu | Bi | Ce | 1080 | 52 | Bi | Ru | Ca | Rh | Eu | La | 260 |
| 53 | In | Zn | La | Eu | Bi | Ce | 1270 | 53 | Re | Zn | Cu | Gd | Eu | La | 850 |
| 54 | Rh | Mn | Fe | Eu | Cu | Ce | 1060 | 54 | Cr | Ni | Fe | Gd | Rh | La | 1330 |
| 55 | Cd | Yb | Ni | La | Fe | Ce | 1290 | 55 | Bi | Cs | Ce | Cu | Fe | La | 2100 |
| 56 | Zn | Ti | Ir | Gd | Fe | Ce | 1120 | 56 | Zn | Ti | In | Ca | Fe | La | 1320 |
| 57 | In | Re | Rh | Ni | Gd | Ce | 570 | 57 | Re | Mn | Cr | Ce | Ca | La | 1020 |
| 58 | Ca | Ru | Rh | La | Ir | Ce | 550 | 58 | Ir | Ru | Cr | Cu | In | La | 1410 |
| 59 | In | Ca | Yb | Ru | Ni | Bi | 330 | 59 | Re | Ir | Cs | Ru | Ce | Eu | 590 |
| 60 | Cd | Re | Zn | Ti | Ni | Bi | 1140 | 60 | Bi | Mn | Zn | Ti | Ce | Eu | 1200 |
| 61 | Ca | Ti | Ir | Eu | Cu | Bi | 850 | 61 | Ir | Ti | In | Gd | Rh | Eu | 1020 |
| 62 | Ti | Ru | Mn | La | Fe | Bi | 2060 | 62 | Ti | Ru | Ni | Cu | Fe | Eu | 510 |
| 63 | In | Cd | Rh | Ir | Fe | Bi | 1730 | 63 | Re | Bi | Cr | In | Fe | Eu | 830 |
| 64 | Ca | Zn | Rh | Mn | Gd | Bi | 860 | 64 | Ir | Zn | Cr | Ni | Ca | Eu | 280 |
| 65 | Re | Yb | La | Ir | Gd | Bi | 330 | 65 | Mn | Cs | Cu | In | Ca | Eu | 920 |
| 66 | In | Zn | Ti | Ru | Rh | Cu | 1210 | 66 | Re | Zn | Ti | Ru | Cr | Rh | 850 |
| 67 | Ca | Cd | Re | Yb | Rh | Cu | 320 | 67 | Ir | Bi | Mn | Cs | Cr | Rh | 710 |
| 68 | In | Ca | La | Gd | Fe | Cu | 1290 | 68 | Re | Ir | Cu | Ca | Fe | Rh | 1510 |
| 69 | Re | Ru | Ni | Ir | Fe | Cu | 500 | 69 | Mn | Ru | Ce | In | Fe | Rh | 700 |
| 70 | Yb | Ti | Ni | Mn | Gd | Cu | 510 | 70 | Cs | Ti | Ce | Ni | Ca | Rh | 1050 |
| 71 | Cd | Zn | Mn | La | Ir | Cu | 860 | 71 | Bi | Zn | Ni | Cu | In | Rh | 1550 |
| 72 | Ca | Re | Ni | Mn | La | Eu | 970 | 72 | Ir | Mn | Ce | Ni | Cu | Gd | 1110 |
| 73 | Ca | Cd | Zn | Ru | Fe | Eu | 1420 | 73 | Ir | Bi | Zn | Ru | Fe | Gd | 760 |
| 74 | In | Re | Yb | Ti | Fe | Eu | 440 | 74 | Re | Mn | Cs | Ti | Fe | Gd | 1270 |
| 75 | Cd | Ti | Rh | La | Gd | Eu | 910 | 75 | Bi | Ti | Cr | Cu | Ca | Gd | 820 |
| 76 | In | Ru | Mn | Ir | Gd | Eu | 890 | 76 | Re | Ru | Ni | In | Ca | Gd | 480 |
| 77 | Zn | Yb | Rh | Ni | Ir | Eu | 440 | 77 | Zn | Cs | Cr | Ce | In | Gd | 970 |

Catalyst mixtures are made up in phenol solvent using the concentrations of each component as given in the rows of TABLE 7. The total volume of each catalyst mixture is 1.0 ml. From each mixture, a 25 microliter aliquot is dispensed into a 2 ml reaction vial, forming a film on the bottom of vials in wells of a reaction plate. The reaction plate is loaded into a reactor and reacted under conditions of the experiment. At the end of the reaction time, the reactor is cooled and depressurized and the contents of each vial are analyzed for diphenyl carbonate product using a gas chromatographic method. Turnover number (TON) for each reaction is calculated as (mols of diphenylcarbonate)/(mols of primary catalyst). The results are given in the column TON of TABLE 7.

Results from the runs are graphed in a normal probability plot. The normal probability plot of the data identifies four positive outliers but no single outstanding result.

A second t-design is generated by randomly permuting the levels of factors of the first run. An experiment according to the design is run. The random design and results are given in Section Run 2 of TABLE 7. A normal probability plot of the Run 2 results shows four positive outliers.

The results of Run 1 and Run 2 are assembled into a 77×77 comparison array. The upper left corner of the comparison array containing the positive outliers is shown in TABLE 8.

TABLE 8

|  |  | Run 1 | | | | |
| --- | --- | --- | --- | --- | --- | --- |
|  | TON | 2060 | 1840 | 1750 | 1730 |
| Run 2 | TON Elements | TiRuMnLaFeBi | CdYbMnEuBiCo | InRuFcCeCrCs | InCdRhIrFeBi |
|  | 2260 BiMnNiCaFeTb | BiFeMn | BiMnYb | 0 | 0 |
|  | 2100 BiCsCeCuFeLa | BiFeLa |  | CsCeFe |  |
|  | 2050 BiMnInGdLaCd | BiMnLa | BiMnCd |  | BiCdIn |
|  | 1930 BiCsTiRuInYb | BiRuTi |  | CsRuIn |  |

A number of common three-way combinations with high TONs are easily identified from the TABLE. These combinations are investigated further. From the results, Bi, Ru and Ti are selected and optimized to a TON exceeding 3000.

While preferred embodiments of the invention have been described, the present invention is capable of variation and modification and therefore should not be limited to the precise details of the Example. The invention includes changes and alterations that fall within the purview of the following claims.

What is claimed is:

1. A method for selecting a best case set of levels of a reaction, comprising;
   defining an experimental space comprising levels of factors according to an incomplete block design and defining an experimental space comprising levels of factors by random selection;
   separately effecting a combinatorial high throughput screening (CHTS) experiment on each experimental space to produce sets of results; and
   selecting common best results from the sets.

2. The method of claim 1, wherein an experimental space comprises levels of factors randomly defined from levels of the incomplete block design.

3. The method of claim 1, further comprising selecting best results from the sets that are common to both sets and defining another experimental space according to the common best results.

4. The method of claim 1, further comprising selecting best results from the sets that are common to both sets and defining another experimental space according to the common best results and effecting another CHTS experiment on the another experimental space to produce a best case set of levels of the reaction.

5. The method of claim 1, wherein results from each CHTS experiment are arranged into separate visual displays that permit identification of best results from each separate experiment.

6. The method of claim 1, wherein the experimental space comprising levels of factors by random selection is defined by an incomplete block comprising randomly selected levels of factors.

7. The method of claim 1, wherein the incomplete block is designated according to t-(ν, κ, λ) where t is the size of an interaction subset, ν is a total number of levels in a design, κ is a block size and λ is a number of times each t-size subset is contained in a set of blocks.

8. The method of claim 7, wherein t is about 3 to about 5, ν is about 8 to about 100, κ is about 4 to about 10 and λ is about 1 to about 5.

9. The method of claim 7, wherein t is about 3 to about 4, ν is about 10 to about 30, κ is about 4 to about 8 and λ is about 1 to about 3.

10. The method of claim 7, wherein t is about 3 to about 4, ν is about 14 to about 26, κ is about 4 to about 6 and λ is about 1 to about 2.

11. The method of claim 7, wherein t is 3, ν is 8, κ is 4 and λ is 1.

12. The method of claim 1, wherein the CHTS experiment comprises steps of;
   preparing a plurality of reagent compositions according to at least one of the experimental spaces;
   formulating a combinatorial library of reactants from said plurality of reagent compositions;
   effecting parallel reaction of the library to produce products; and
   evaluating the products to select a lead from the library of reactants.

13. The method of claim 1, wherein conducting the CHTS experiment comprises providing a reactor plate comprising a substrate with an array of reaction cells containing at least one reactant according to at least one of the experimental spaces and reacting the reactant in parallel with other reactants.

14. The method of claim 1, wherein the CHTS comprises effecting parallel chemical reactions of an array of reactants defined according to at least one of the experimental spaces.

15. The method of claim 1, wherein the CHTS comprises effecting parallel chemical reactions on a micro scale on reactants defined according to at least one of the experimental spaces.

16. The method of claim 1, wherein the CHTS comprises an iteration of steps of simultaneously reacting a multiplicity of tagged reactants and identifying a multiplicity of tagged products of the reaction and evaluating the identified products after completion of a single or repeated iteration.

17. The method of claim 1, wherein the experimental space factors comprise reactants, catalysts and conditions and the CHTS comprises
   (A)(a) reacting a reactant selected according to at least one of the experimental spaces under a selected set of catalysts or reaction conditions; and (b) evaluating a set of results of the reacting step; and
   (B) reiterating step (A) wherein a selected experimental space selected for a step (a) is chosen as a result of an evaluating step (b) of a preceding iteration of step (A).

18. The method of claim 1, wherein the factors include a catalyst system comprising a Group VIII B metal.

19. The method of claim 1, wherein the factors include a catalyst system comprising palladium.

20. The method of claim 1, wherein the factors include a catalyst system comprising a halide composition.

21. The method of claim 1, wherein the factors include an inorganic co-catalyst.

22. The method of claim 1, wherein the factors include a catalyst system includes a combination of inorganic co-catalysts.

23. The method of claim 1, wherein the factors comprise a reactant or catalyst at least partially embodied in a liquid and effecting the CHTS method comprises contacting the reactant or catalyst with an additional reactant at least partially embodied in a gas, wherein the liquid forms a film having a thickness sufficient to allow a reaction rate that is essentially independent of a mass transfer rate of additional reactant into the liquid to synthesize products that comprise the results.

24. A combinatorial high through put screening (CHTS) method comprising:

(1) selecting factors for an experimental space;

(2) selecting a degree of interaction (t) of the factors;

(3) selecting a degree of replication ($\lambda$);

(4) selecting a block size ($\kappa$);

(5) generating an experimental incomplete block design according to t, $\lambda$ and $\kappa$;

(6) conducting a CHTS method according to the design;

(7) randomly permuting levels of the factors in the design;

(8) conducting a second CHTS method according to the permuted levels design; and (9) identifying common levels from the experiments that represent best results.

25. The method of claim 24, wherein the common levels are identified by arranging the results of the two experiments in a visual aid.

26. The method of claim 24, wherein the common levels are identified by arranging the results of the two CHTS methods as two converging vectors.

27. The method of claim 24, wherein the common levels are identified by arranging the results of the two CHTS methods as an array that displays common best results in a designated array section.

28. A system for conducting an experiment, comprising;

a reactor for effecting a combinatorial high through put screening (CHTS) method on an experimental space to produce results; and a programmed controller for the reactor that defines an experimental space comprising levels of factors according to an incomplete block design and defines an experimental space comprising levels of factors by random selection.

29. The system of claim 28, wherein the randomly defined experimental space comprises levels of factors randomly defined from levels of the incomplete block design.

30. The method of claim 1, wherein the controller selects best common results from sets of results from CHTS methods effected in the reactor and defines another experimental space according to the common best results.

31. The system of claim 28, wherein the controller is a computer, processor or microprocessor.

32. The system of claim 28, further comprising a dispensing assembly to charge factor levels of reactants or catalysts representing the catalyzed chemical experimental space to wells of an array plate for charging to the reactor.

33. The system of claim 28, wherein the dispensing assembly is controlled by the controller to charge factor levels of reactants or catalysts according to the controller defined space.

34. The system of claim 28, further comprising a detector to detect results of the CHTS method effected in the reactor.

* * * * *